(12) United States Patent
Bossart et al.

(10) Patent No.: US 6,480,795 B1
(45) Date of Patent: Nov. 12, 2002

(54) AUTOMATIC CALIBRATION METHOD

(75) Inventors: Roman Bossart, Flawil (CH); Jörg Grabinski, Niederuzwil (CH)

(73) Assignee: Buchi Labortechnik AG, Flawil (CH)

( * ) Notice: Subject to any disclaimer, the term of this patent is extended or adjusted under 35 U.S.C. 154(b) by 0 days.

(21) Appl. No.: 09/623,469

(22) PCT Filed: Sep. 30, 1998

(86) PCT No.: PCT/CH98/00418

§ 371 (c)(1),
(2), (4) Date: Jan. 18, 2001

(87) PCT Pub. No.: WO99/47909

PCT Pub. Date: Sep. 23, 1999

(30) Foreign Application Priority Data

Mar. 13, 1998 (DE) .......................... 198 10 917

(51) Int. Cl.[7] .............................. G01N 21/27
(52) U.S. Cl. .................... 702/104; 382/158; 702/27
(58) Field of Search ................... 702/104, 27; 250/282, 250/288; 703/6; 382/158

(56) References Cited

U.S. PATENT DOCUMENTS

| 5,335,291 A | * | 8/1994 | Kramer et al. | 382/158 |
| 5,592,402 A | * | 1/1997 | Beebe et al. | 700/266 |
| 5,672,869 A | * | 9/1997 | Windng | 250/282 |

FOREIGN PATENT DOCUMENTS

WO    WO 9706418    *  2/1997

* cited by examiner

*Primary Examiner*—Kamini Shah
(74) *Attorney, Agent, or Firm*—Shoemaker and Mattare (57) ABSTRACT

The invention relates to an automatic calibration method related to spectra of a spectrometer for examining substances in the pharmaceutical, chemical, cosmetic, dye, plastics, rubber, and foodstuff industries.

5 Claims, 8 Drawing Sheets

AUTOMATIC CALIBRATION METHOD

BACKGROUND OF THE INVENTION

The invention relates to a calibration method for evaluating spectra of a spectrometer for examining solid, liquid or gaseous substances.

This calibration method involves the analysis of spectra produced by way of a spectrometer. Such analysis methods and devices function according to the principle whereby a transmitter emits electromagnetic radiation onto the substance to be examined and those rays which are reflected by or penetrate through the substance are recorded by a receiver. For these examinations all wavelength regions of the electromagnetic spectrum may be used. Particularly suitable is the wave region in the near infra-red (NIR). Such methods and devices are among those mentioned in CH 685807 A5 or CH 683713 A5.

This analysis method is applied in particular in the pharmaceutical, chemical, cosmetic, colouring, plastics, rubber and foodstuffs industries.

Since with this spectral method there are various instrument types, sensors, substance types, aggregate conditions, mathematical methods and calibration behaviour and for each substance to be examined there are nominal spectra, calibration is required before the actual evaluation.

Until now the calibration was effected by time-consuming, empirical, intuitive or "guessing" determination of the required variables cited above.

SUMMARY OF THE INVENTION

The object of the present invention is to specify a calibration method which automatically in as short a time as possible ascertains the optimal boundary conditions of the actual evaluation method.

According to the invention this object is achieved by the method described below, wherein the calibration is effected automatically.

Furthermore with the calibration method according to the invention the structure of a knowledge base which contains all data, expert knowledge, and their weightings may be developed.

For calibration further there serve the nominal spectra known for a substance to be examined.

The measured spectra are generally characterised by a multitude of oscillation superpositions. A visual evaluation is therefore practically not possible. Specific differences in the spectra of similar substances often consist only of a slight displacement or small shape changes of the mostly wide absorption bands. It is therefore necessary to evaluate these spectra with mathematical methods. These mathematical methods are based on chemometric software. Chemometry is to be understood as the application of mathematical methods in chemistry. The chemometric software in spectroscopy has the exercise of finding a statistical relationship between spectral data and the known property values of the samples used for calibration.

BRIEF DESCRIPTION OF THE DRAWINGS

As an example, in the following, the invention is represented in the form of flow diagrams.

DESCRIPTION OF THE PREFERRED EMBODIMENTS

Figure 1:
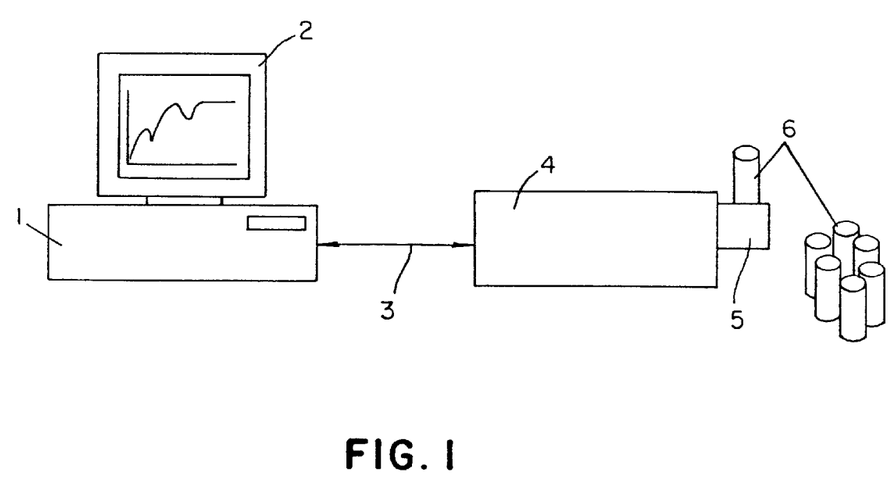
FIG. 1 is a schematic representation of a possible measuring device.

FIG. 1 represents a possible measuring arrangement. The samples 6 are acquired by a measuring head 5 containing a sensor 5, wherein a spectrometer 4 records the spectra. The digitalised data are via a lead 3 led into a computer 1 which then carries out the calibration according to the invention. The spectra and the evaluation is usually displayed on a monitor 2.

Figure 2:
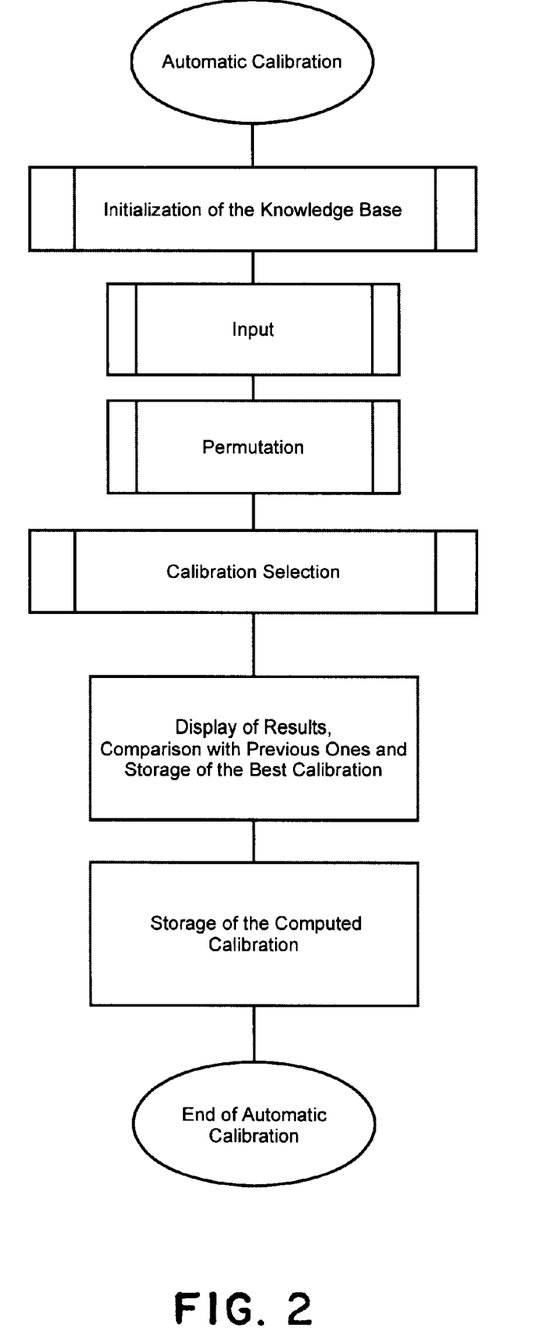
FIG. 2 is a flow diagram of the automatic calibration.

FIG. 2 shows the basic course of the automatic calibration according to the invention. The first step comprises the initialisation of the knowledge base. There follows the actual input of the data with the formation of data sets. The components of the data sets are completely or partly permutated and are subjected to a computing method. The used permutations are initialised, wherein for each permutation a special factor selection, a Q-value is computed and thus a specific calibration is allocated and stored. There results therefrom a multitude of quality values from which the optimal Q-value may be selected and thus the most suitable calibration may be determined.

Figure 3:
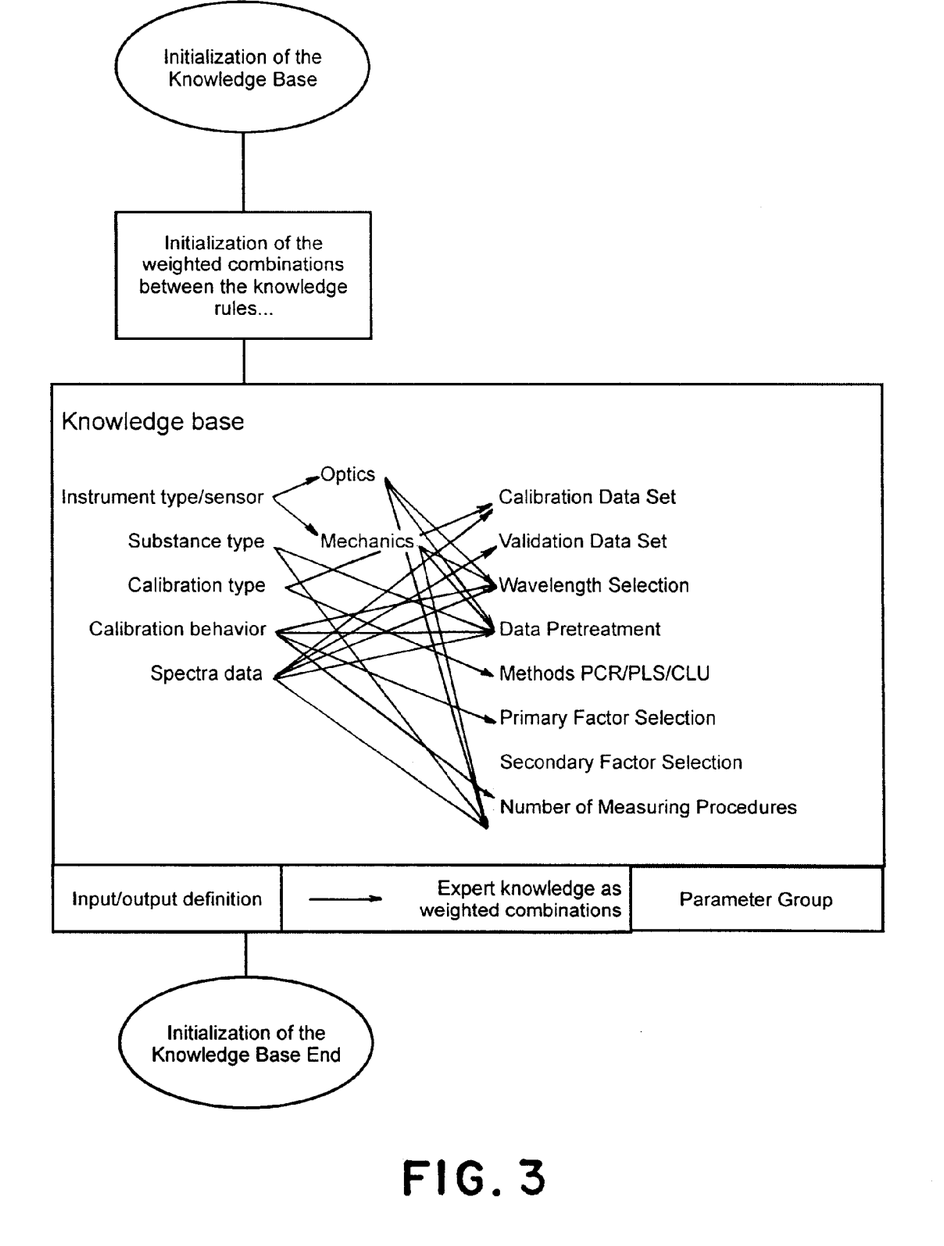
FIG. 3 shows initialisation of the knowledge base.

FIG. 3 represents the initialisation of the knowledge base. The knowledge base forms the basis for the components containing the data sets. To the initial data there belong for example the instrument type/sensor, the substance type, the calibration type, the calibration behaviour and/or spectral data. From these five initial data, on account of expert knowledge the parameter group is determined and weighted. As a sensor type an optical or mechanical sensor may be considered. The substance type is determined by way of a prior treatment of data and by way of the selection of the measuring procedures. To the calibration type there belongs a calibration data set with a possible computing method. The calibration behaviour is determined from the selected wavelength region, a pre-treatment of data, the primary, the secondary factors and/or the number of measuring procedures. The spectra data are composed of the calibration data set, the validation data set, the wavelength selection, the pretreatment of data and/or the number of measuring procedures.

Figure 4:
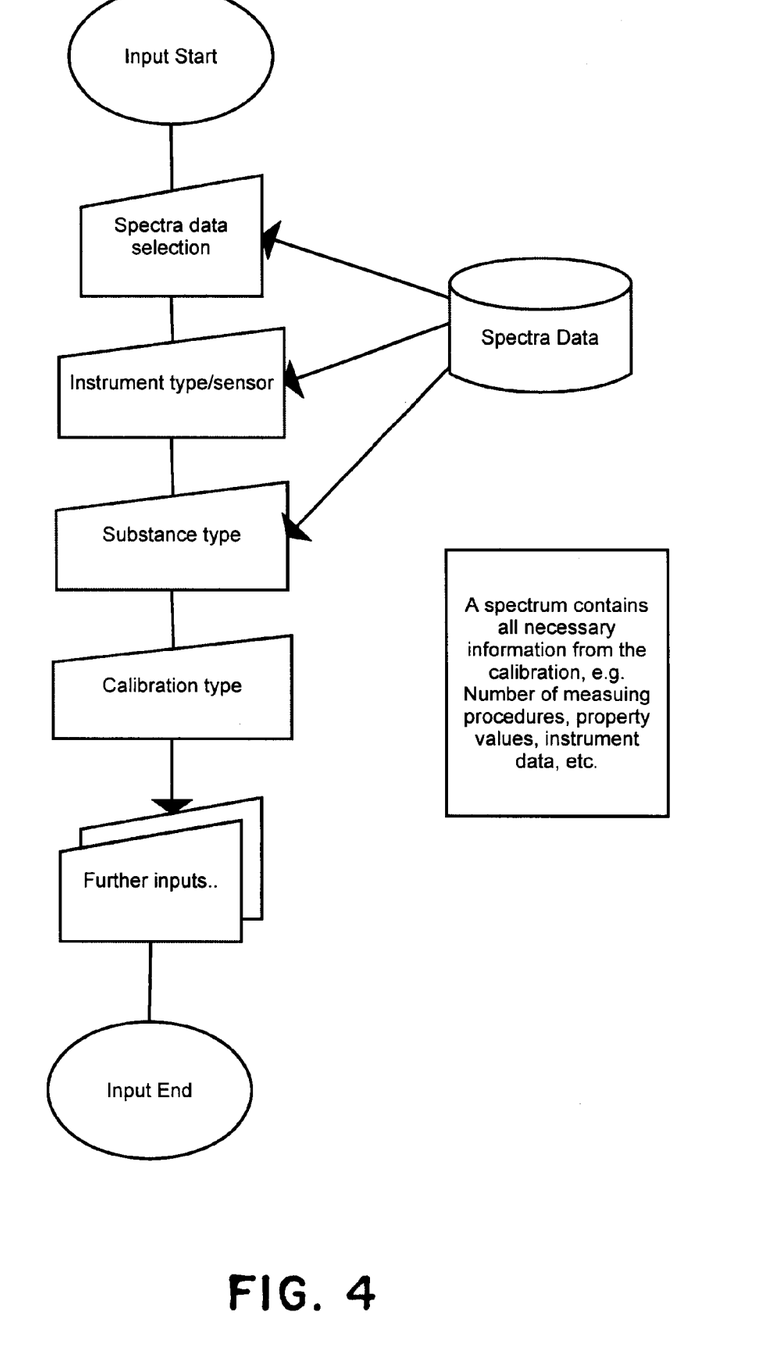
FIG. 4 shows an input step.

After the initialisation there follows the actual input according to FIG. 4. From the spectra data there is selected in particular the instrument type/sensor with which the respective spectrum is recorded. Furthermore the substance type, the calibration type and the calibration behaviour are inputted.

Figure 5:
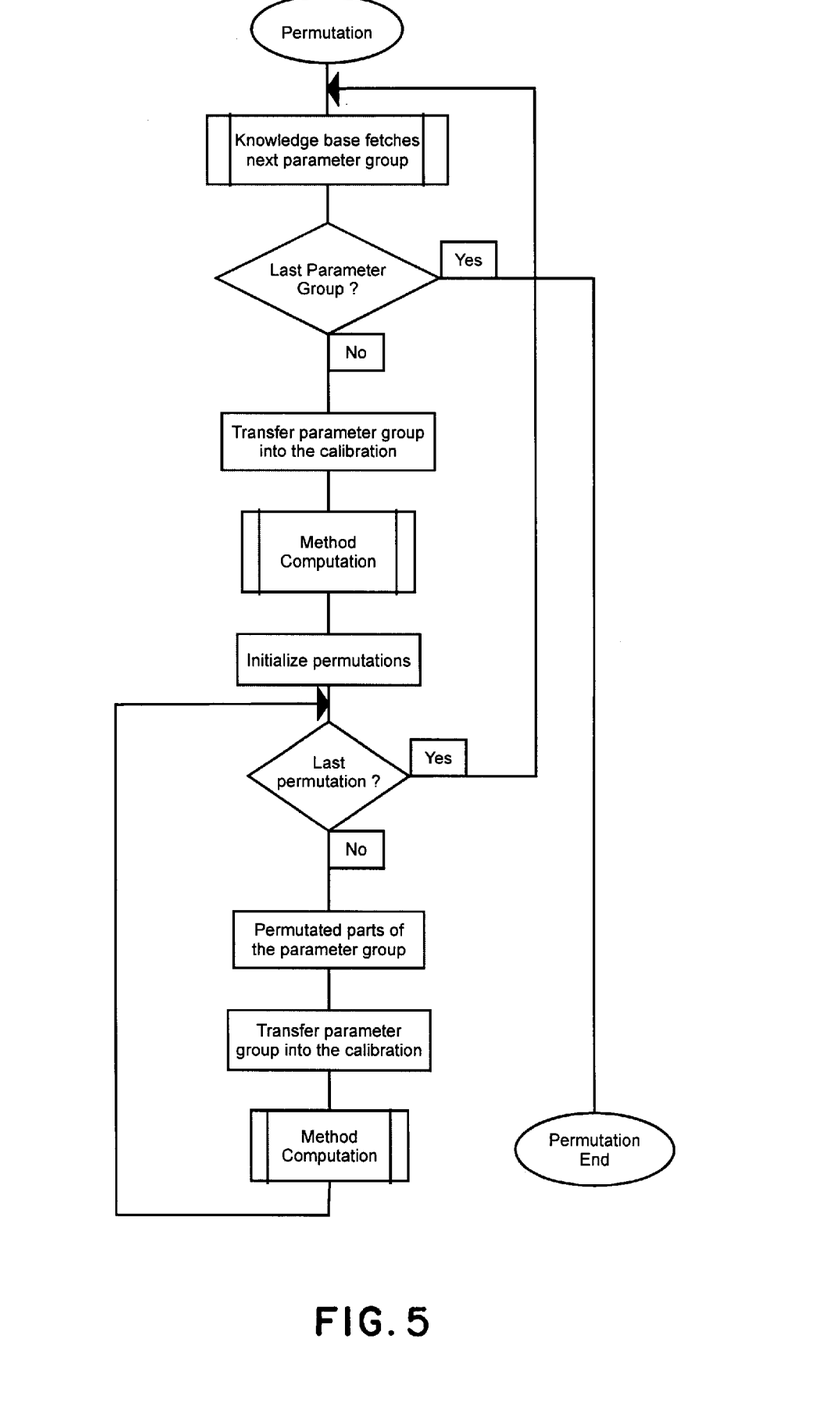
FIG. 5 shows a permutation step.

After the input there follows according to FIG. 5 the complete and/or part permutation of the components of the data sets. The respective parameter group is subjected to a computation for the calibration. With this, the method itself forms a component of the data set. The method computation is broken down in FIG. 6.

Figure 6:
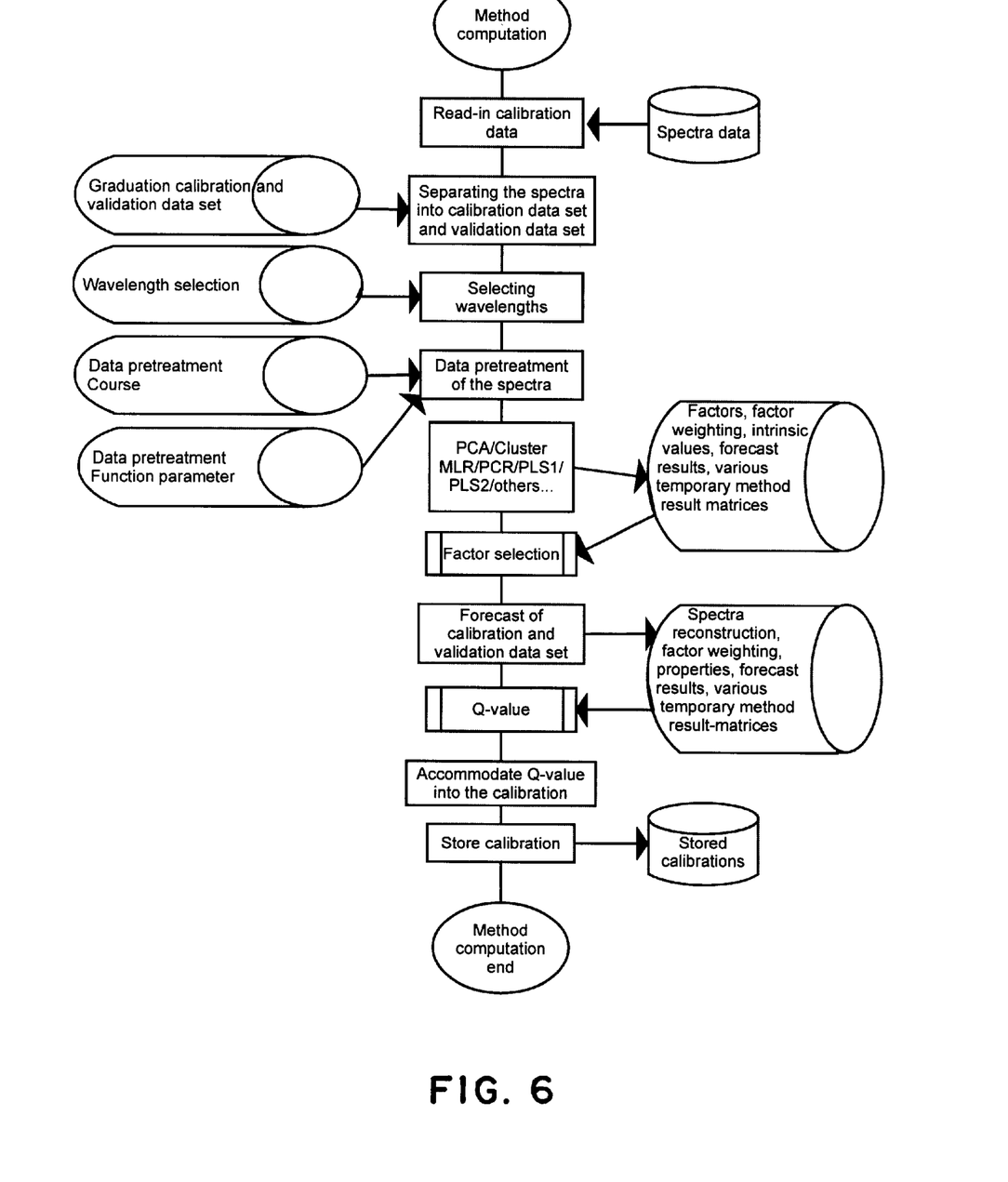
FIG. 6 shows the method computation.

The computation course begins with the main component analysis, amongst others published in S. Wood, K. Esbensen, P. Geladi, "Principle Component Analysis", Chemometrics and Intelligent Laboratory Systems 2 (1987) 37–52. A spectrum measured with the device according to FIG. 1 may for example be composed of for example 500 measuring points. This individual measuring data corresponds to the intensity values in dependence on 500 wave numbers in the near infrared. In order to obtain a good calibration, one in turn requires a large number of spectra. For example 100 substance spectra thus result in 50,000 data points which entails a great computing effort. In order to obtain acceptable computing times the spectral data is condensed with the help of the main component analysis. With this no important information is lost.

With a calibration, to the samples there are allocated two different data sets independent of one another, specifically the calibration data set on the one hand and the validation data set on the other hand. With the calibration data set the main component analysis is carried out. With the validation data set the results of the calibration are evaluated.

For the quantitative calibration there are available a multitude of computation methods. In particular there are cited here the three most common computation methods: Multiple Linear Regression (MLR), Principle Component Regression (PCR) and the Partial Least Squares Regression (PLS), for example published in Bruce R Kowalski, "Chemometrics, Mathematics & Statistics in Chemistry" NATO AIS Series, Series C: Math. & Phys. Sciences Vol. 138 (1984).

MLR is an extension of the linear regression to several dimensions. This evaluation on account of a few selective wavelengths requires no main component analysis. In this method the properties are computed by intensity values and correlation coefficients.

The PCR is composed of two steps. In the first step the intensities to be loaded are computed by way of the main component analysis. The second step produces the correlation coefficients by way of MLR.

According to the principle of recursion with PLS the data to be loaded is computed. The quantitative reference values are however taken account of already at the beginning of the computation. Whilst the PCR reduces the spectral data to the most dominant dimensions, the PLS targets the most relative dimensions, i.e. the best agreement between prognosed and actual values.

The actual calibration is made up on the one hand of the qualitative and on the other hand of the quantitative calibration.

The course of the quantitative calibration begins with the measuring of the calibration spectra. In order to set up a representative calibration a multitude of various charges of the same class should be measured. With an increasing number of measuring run-throughs the signal/optical noise ratio may be improved and inhomogenities compensated. After the measuring of the samples, the actual setting up of the calibration begins.

Figure 7:
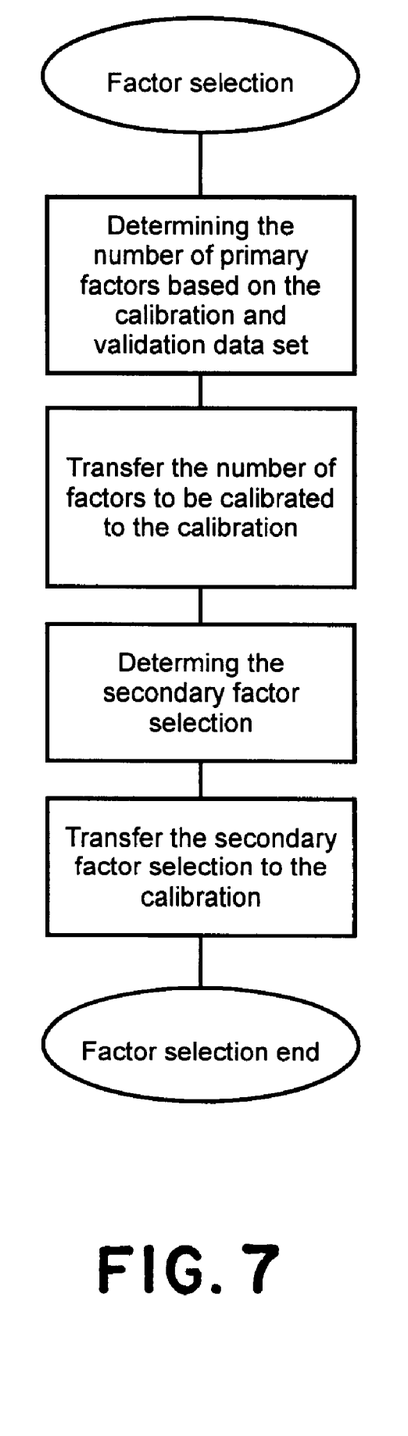
FIG. 7 shows a factor selection step.

1. The spectra are divided into a calibration data set and into a validation data set, wherein the selection is effected purely randomly. As mentioned above, the calibration data set must be independent from the validation data set. In this first set one works without a wavelength selection and without data pretreatment.
2. The main component analysis is carried out.
3. The total number of the primary factors is selected. Primary factors are to be understood as the factors which are meaningful for the description of the spectra up to the optical noise limit of the applied measuring method.
4. Following the determination of the primary factors, the selection factors, called secondary factors are selected. These selection factors are the factors which allocate to the associated spectra an unequivocal separation of the various calibration qualities. The factor selection is shown in the form of a flow diagram in FIG. 7.
5. There follows an optimisation of the calibration. If no selection is achieved the various data pretreatments should be carried out. Those wavelength regions are rejected which do not contain any significant information.
6. The best calibration is then stored and tested.

The qualitative calibration is used for measuring property values (e.g. water content, mixing constituent parts, hydroxy number, etc.).

After measuring the samples the calibration is set up. It is effected essentially according to the same course as with the qualitative calibration.

Figure 8:
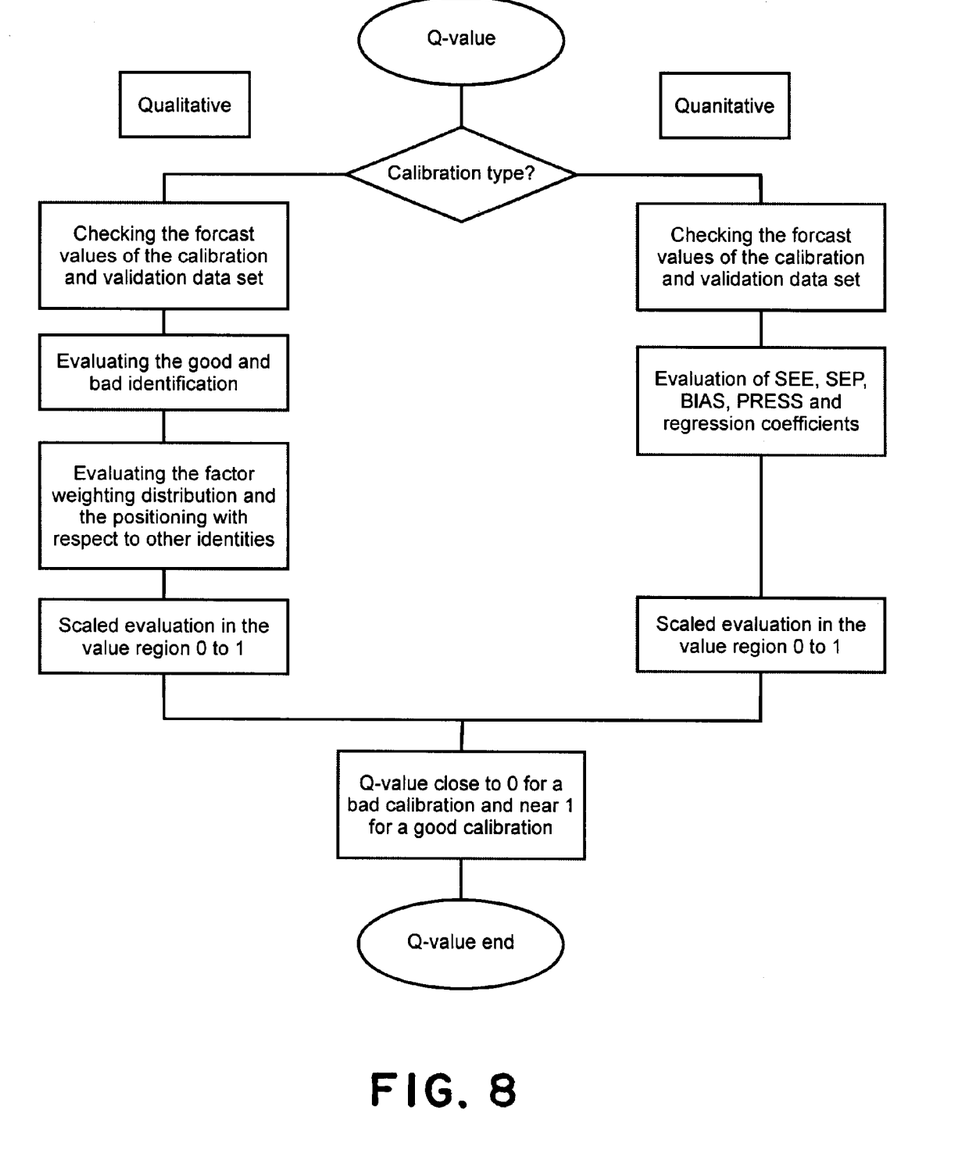
FIG. 8 illustrates qualitative and quantitative Q-value determination

According to the type of calibration, qualitative or quantitative, according to the flow diagram in FIG. 8, the quality of the calibration, the so-called Q-value, is determined.

At the end of the calibration computations subsequently a table of the various Q-values is set up from which one may then select the optimal calibration.

What is claimed is:

1. A method for automatically calibrating a spectrometer for evaluating spectra in the course of examination of solid, liquid or gaseous substances, said method comprising the steps of
    (a) acquiring a plurality of reference spectra of a plurality of samples,
    (b) storing said spectra in a spectral matrix,
    (c) treating said data and reducing the dimension of said matrix by at least one of
        (1) pretreating the data with a mathematical method,
        (2) selecting a specific wavelength, and
        (3) reducing the amount of data by application of a calibration method selected from the principal component analysis (PCA), PCR or PLS, thereby forming a first set of treated data and a first calibration model,
    (d) determining a first quality value of a calibration on the basis of said first set of treated data,
    (e) repeating the treating and determining steps for all possible permutations of pretreatment methods, wavelength ranges, and calibration methods, thereby forming repsective quality values,
    (f) selecting an appropriate calibration model on the basis of the best quality values.

2. The method of claim 1, comprising additional steps of selecting a plurality of secondary factors, and including the secondary factors in the possible permutations in step (e).

3. The method of claim 1, further comprising a preselection step wherein possible mathematical methods, wavelength ranges, and primary and secondary factors are selected or excluded on the basis of the sensor type used and the substance to be examined.

4. A method according to claim 1, characterised in that the optimal number of primary factors for describing the spectra is determined up to the optical noise limit of the applied measuring method.

5. A method according to claim 1, characterised in that after the determining of the number of primary factors the selection factors described as secondary factors are determined which permit an unequivocal separation of the various Q-values of the calibrations.

* * * * *